(12) United States Patent
Zhong et al.

(10) Patent No.: US 6,368,356 B1
(45) Date of Patent: Apr. 9, 2002

(54) MEDICAL DEVICES COMPRISING HYDROGEL POLYMERS HAVING IMPROVED MECHANICAL PROPERTIES

(75) Inventors: Sheng Ping Zhong, Northboro; Arthur R. Madenjian, Winchester; Douglas E. Godshall, Franklin, all of MA (US); John M. Ronan; Samuel A. Thompson, both of Wilmington, DE (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/512,698

(22) Filed: Feb. 25, 2000

Related U.S. Application Data (63) Continuation-in-part of application No. 09/496,709, filed on Feb. 2, 2000, now Pat. No. 6,184,266, which is a continuation of application No. 08/679,609, filed on Jul. 11, 1996, now Pat. No. 6,060,534.

(60) Provisional application No. 60/122,256, filed on Feb. 25, 1999, and provisional application No. 60/122,176, filed on Feb. 25, 1999.

(51) Int. Cl.$^7$ ............................. A61F 2/04; A61F 2/06; A61M 25/00; C08J 3/24

(52) U.S. Cl. .................. 623/23.75; 623/1.18; 623/1.19; 623/1.49; 623/925; 623/926; 604/264; 424/78.17; 424/422; 523/105; 523/113; 523/124; 524/28; 524/43; 524/44; 524/45; 524/47; 524/503; 524/918; 525/903

(58) Field of Search ................................. 523/113, 105; 524/503, 916, 28, 47, 43, 44, 45; 525/903; 424/78.17, 422; 604/264; 623/1.49, 23.75, 925, 926, 1.18, 1.19

(56) References Cited

U.S. PATENT DOCUMENTS

| | | |
|---|---|---|
| 2,485,512 A | 10/1949 | Rose |
| 2,541,804 A | 2/1951 | Wormell |
| 2,712,672 A | 7/1955 | Calcagno |
| 2,847,713 A | 8/1958 | Weingand |
| 2,897,547 A | 8/1959 | Weingand |
| 3,271,496 A | 9/1966 | Michaels |
| 4,137,921 A | 2/1979 | Okuzumi et al. |
| 4,286,341 A | 9/1981 | Greer et al. |
| 4,339,295 A | 7/1982 | Boretos et al. |
| 4,439,322 A | 3/1984 | Sonoda et al. |
| 4,582,865 A | 4/1986 | Balazs et al. |
| 4,605,691 A | 8/1986 | Balazs et al. |
| 4,613,517 A | 9/1986 | Williams et al. |
| 4,636,524 A | 1/1987 | Balazs et al. |
| 4,650,488 A | 3/1987 | Bays et al. |
| 4,716,154 A | 12/1987 | Malson et al. |
| 4,716,224 A | 12/1987 | Sakurai et al. |
| 4,801,475 A | 1/1989 | Halpern et al. |
| 4,814,120 A | 3/1989 | Huc et al. |
| 4,838,876 A | 6/1989 | Wong et al. |
| 4,851,521 A | 7/1989 | della Valle et al. |
| 4,863,907 A | 9/1989 | Sakurai et al. |
| 4,878,907 A | 11/1989 | Okada et al. |
| 4,888,016 A | 12/1989 | Langerman |
| 4,902,295 A | 2/1990 | Walthall et al. |
| 4,906,237 A | 3/1990 | Johansson et al. |
| 4,923,645 A | 5/1990 | Tsang et al. |
| 4,941,870 A | 7/1990 | Okada et al. |
| 4,957,744 A | 9/1990 | della Valle et al. |
| 4,965,353 A | 10/1990 | della Valle et al. |
| 4,997,443 A | 3/1991 | Walthall et al. |
| 5,057,606 A | 10/1991 | Garbe |
| 5,061,738 A | 10/1991 | Solomon et al. |
| 5,077,352 A | 12/1991 | Elton |
| 5,085,629 A | 2/1992 | Goldbert et al. |

(List continued on next page.)

FOREIGN PATENT DOCUMENTS

| | | |
|---|---|---|
| DE | 2827289 | 1/1979 |
| EP | 0065884 | 12/1982 |
| EP | 0213908 A2 | 3/1987 |
| EP | 0271216 A2 | 6/1988 |
| EP | 0341745 | 11/1989 |
| EP | 080254 A2 | 8/1990 |
| EP | 0454373 A2 | 10/1991 |
| EP | 0507604 A2 | 10/1992 |
| EP | 0645150 | 3/1995 |
| GB | 2151244 A | 7/1985 |
| JP | 04145218 | 5/1992 |
| WO | 89/05671 | 6/1989 |
| WO | 90/10020 | 9/1990 |
| WO | 91/07200 | 5/1991 |
| WO | 92/13579 | 8/1992 |
| WO | 92/18098 | 10/1992 |
| WO | 93/09176 | 5/1993 |

OTHER PUBLICATIONS

Andrade, Joseph D., "Hydrogels for Medical and Related Applications", Aug. 27–28, 1975, pp. 1–36 (Editor, presented article at that time); AM. Chem. Soc. 1976.

Kocvara et al., "Gel–Fabric Prostheses of the Ureter", *Journal of Biomedical Research*, vol. 1, pp. 325–336 (1967).

Ross, "Living Cure" (Science and the Citizen), *Scientific American*, Jun. 1993, pp. 18–23.

*Primary Examiner*—Peter Szekely
(74) *Attorney, Agent, or Firm*—Testa, Hurwitz & Thibeault, LLP

(57) ABSTRACT

The invention provides a means of boosting the mechanical performance of shaped shaped medical devices comprising polymer hydrogels, such as stents, so that they may be more easily inserted into or removed from the body. In one aspect, the invention provides shaped medical devices having increased mechanical strength and comprising both ionic and covalent crosslinks. In another aspect, the invention provides a shaped medical device having a heterogeneous polymer composition and a variable dissolution or degradation rate along its length. The shaped medical devices according to the present invention retain their shape and stiffness during insertion into the body and can swell and soften inside the body to enhance patient comfort.

38 Claims, 2 Drawing Sheets

U.S. PATENT DOCUMENTS

| | | |
|---|---|---|
| 5,089,606 A | 2/1992 | Cole et al. |
| 5,128,326 A | 7/1992 | Balazs et al. |
| 5,149,543 A | 9/1992 | Cohen et al. |
| 5,202,431 A | 4/1993 | della Valle et al. |
| 5,278,201 A | 1/1994 | Dunn et al. |
| 5,298,569 A | 3/1994 | Yamamori et al. |
| 5,302,393 A | 4/1994 | Matsumoto et al. |
| 5,306,764 A | 4/1994 | Chen |
| 5,308,701 A | 5/1994 | Cohen et al. |
| 5,322,935 A | 6/1994 | Smith |
| 5,328,939 A * | 7/1994 | Smith ........................ 521/187 |
| 5,334,640 A | 8/1994 | Desai et al. |
| 5,413,782 A | 5/1995 | Warchol et al. |
| 5,514,377 A | 5/1996 | Cochrum et al. |
| 5,531,716 A | 7/1996 | Luzio et al. |
| 5,532,305 A | 7/1996 | Matsuzaki et al. |
| 5,554,388 A | 9/1996 | Illum |
| 5,650,116 A * | 7/1997 | Thompson .................. 264/561 |
| 5,736,595 A * | 4/1998 | Günther et al. ............... 524/28 |
| 6,096,018 A * | 4/2000 | Luzio et al. ................ 604/500 |
| 6,126,645 A * | 10/2000 | Thompson .................. 604/245 |

\* cited by examiner

MEDICAL DEVICES COMPRISING HYDROGEL POLYMERS HAVING IMPROVED MECHANICAL PROPERTIES

RELATED APPLICATIONS

This application is a continuation-in-part of U.S. patent application Ser. No. 09/496,709, filed Feb. 2, 2000, now U.S. Pat. No. 6,184,266, which is a continuation of U.S. patent application Ser. No. 08/679,609, filed Jul. 11, 1996 now U.S. Pat. No. 6,060,534. This application also claims priority to U.S. Provisional Applications Ser. Nos. 60/122,256, filed Feb. 25, 1999, and 60/122,176, filed Feb. 25, 1999. The entirety of these applications is incorporated herein by reference.

FIELD OF THE INVENTION

This invention relates to shaped medical devices comprising polymer hydrogels having improved mechanical properties. More particularly, the invention relates to shaped medical devices which can function as temporary implants which do not require additional surgical procedures for removal.

BACKGROUND OF THE INVENTION

Shaped medical devices for insertion and/or implantation into the body have a variety of applications including drug delivery, tissue engineering, vascular surgery (e.g., angioplasty) and drainage (e.g., from the kidney). Such devices include vascular grafts, stents, catheters, cannulas, plugs, constrictors, tissue scaffolds, and tissue or biological encapsulants, and the like.

Typically, many of these devices are made of durable, non-degradable plastic materials such as polyurethanes, polyacrylates, silicone polymers, and the like. Typical stents, for example, are permanent devices which require a surgical procedure to remove and may cause discomfort. Shaped medical devices have also been disclosed which are made from biodegradable polymers. These remain stable in vivo for a period of time but eventually biodegrade into small fragments which are removed by the body by normal elimination in the urine or feces. In the case of ureteral stents, the fragmentation of such biodegradeable polymers into small pieces can obstruct the ureter and cause patient discomfort.

Typical biodegradable polymers used in these devices include polyesters, polyanhydrides and polyorthoesters which undergo hydrolytic chain cleavage, as disclosed in U.S. Pat. No. 5,085,629, crosslinked polysaccharide hydrogel polymers as disclosed in U.S. Pat. No. 5,057,606, and other ionically crosslinked hydrogels, as disclosed in U.S. Pat. Nos. 4,941,870, 4,286,341 and 4,878,907, the entirety of which are incorporated herein by reference. Crosslinked polysaccharide hydrogel polymers also are disclosed in EPA 0507604 A2.

EPA 0645150 A-1 describes hydrogel medical devices prepared from ionically crosslinked anionic polymers (e.g., polysaccharides such as calcium alginate) or ionically crosslinked cationic polymers (e.g., chitosan, cationic guar, cationic starch, and polyethylene amine). These devices can be rapidly disintegrated in vivo upon the administration of a chemical trigger material which displaces the crosslinking ions.

Hydrogels are water-swollen polymers which offer excellent biocompatibility and have a decreased tendency to induce thrombosis, encrustation, and inflammation. Unfortunately, the use of hydrogels in medical device applications has often been hindered by poor mechanical performance. Although many medical device applications for hydrogels exist where minimal stresses are encountered by the device in vivo, most applications require that the device survive high stresses during implantation. Inferior mechanical properties result from the swollen nature of hydrogels and the non-stress bearing nature of the swelling agent (e.g., aqueous fluids). Hydrogels suffer from low modulus, low yield stress, and low strength, when compared to non-swollen polymer systems.

In addition, ion sequestrants within certain body fluids, such as the urine, will degrade the hydrogel too quickly, preventing the use of such hydrogels in ureteral stent applications since a hydrogel stent will not hold its strength long enough to allow the device to function. Further, the amount of sequestrants in the urine is very difficult to control, even with the use of certain diets. As a result, the performance of a hydrogel stent in the ureter is variable from patient to patient.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 4A shows suture material extruded with the hydrogel throughout the length of the stent. FIG. 4B shows suture material extruded with the hydrogel only within the tubular body of the stent.

SUMMARY OF THE INVENTION

There is a need in the art to provide shaped medical devices comprising hydrogels which offer biological compatibility without sacrificing desired mechanical properties, such as strength and modulus properties. The present invention provides a means of boosting the mechanical performance of shaped medical devices comprising hydrogels, so that they may be more easily inserted into the body. At the same time the invention provides a means to soften such devices in vivo while retaining the structural integrity of the device, allowing the device to remain implanted within the body with minimal patient discomfort.

In one aspect, the invention provides a shaped medical device having increased mechanical strength and comprising both ionic and covalent crosslinks. The shaped medical device according to the invention comprises a shape memory, allowing the device to be reversibly shaped in different conformations for ease of implantation and removal from the body. In one embodiment of the invention, the shaped medical device has sufficient mechanical strength to permit the flow of fluids (e.g., blood) through the device. In another embodiment of the invention, the shaped medical device is conformable to the shape of a stent, catheter, cannula, plug, filler, constrictor, bone anchor, plate, rod, seed, sheet or tube. In one embodiment, a shaped medical device in the form of a sheet is provided as a coating for another medical device. In this embodiment; the underlying medical device may comprise a dissolvable polymer, a non-dissolvable polymer, or combination non-dissolvable and dissolvable polymers.

The shaped medical device may comprise additives to enhance the desired properties of the device. In one embodiment, the shaped medical device comprises radiopaque fillers to allow visualization of the device within the body, both during and after placement at a desired target site. Additional fillers to increase the mechanical strength of the device may also be provided, including pieces of non-hydrogel material, such as suture material, or other non-dissolvable materials. In one aspect of the invention, the shaped medical device comprises an additive for medical treatment selected from the group consisting of an antiseptic, an antibiotic, an anticoagulant, a contraceptive, a nucleic acid molecule, a protein, and a medicine. In a further embodiment of the invention, the shaped medical device is seeded with cells.

In one embodiment of the invention, the shaped medical device comprising additives is provided in the form of a sheet which may be applied to a localized target site within or on the body (e.g., as a patch or a dressing) to achieve a biological effect at that target site. In another embodiment, the sheet is provided as a coating to another medical device which is implanted at a target site.

Crosslinks may be distributed homogeneously or heterogeneously throughout polymer that forms the shaped medical device. In one embodiment of the invention, a shaped medical device comprises a polymer having a heterogeneous distribution of non-ionic and ionic crosslinks and a variable dissolution or degradation rate along its length. In another embodiment of the invention, the shaped medical device comprises alternating segments of ionically crosslinked and non-ionically crosslinked polymer. The length of a segment may be varied to adapt the shaped medical device to a pre-selected dissolution and/or degradation rate. In still a further embodiment of the invention, segments of non-dissolvable polymer are included. In this embodiment, the non-dissolvable polymer may be in the form of a string or a mesh.

In one aspect, the invention provides a shaped medical device in the form of a sheet which covers another medical device. In another aspect, the sheet-shaped medical device has a different dissolution rate from the underlying medical device. In a further embodiment of the invention, the sheet-shaped medical device comprises an additive (e.g., a medicine or drug) and dissolves more quickly than the underlying medical device, allowing drug release to occur while maintaining the structural integrity of the underlying device.

The shaped medical devices according to the present invention retain their shape and stiffness during insertion into the body (e.g., by delivery through an endoscope) and can swell and soften inside the body to enhance patient comfort. In still another embodiment, the shaped medical device may be strengthened prior to removal from the body.

Description

This invention relates to shaped medical devices comprising polymer hydrogels having improved mechanical properties. More particularly, the invention relates to devices which can function as temporary implants which do not require additional surgical procedures for removal. The teachings of the present invention may be adapted for a variety of shaped medical devices which may be used for insertion and/or implantation into the body, including, but not limited to, biliary, urinary or vascular stents, catheters, cannulas, or components thereof, plugs or fillers, coatings, constrictors, bone anchors (e.g., screws), bone grafts (e.g., plates and rods), seeds or capsules, patches, or dressings, skin, and matrices for tissue engineering (e.g., sheets, tubes, plugs, and other macroscopic shapes). In one embodiment of the invention, the shaped medical devices are optionally seeded with differentiated cells or stem cells. The medical devices according to the invention are suitable for both human and animal use.

The invention is particularly applicable to shaped medical devices of tubular configuration which come in contact with one or more body fluids, such as blood, urine, gastrointestinal fluids, and bile. The shaped medical devices are particularly applicable for use in gastrointestinal, urogenital, cardiovascular, lymphatic, otorhinolaryngological, optical, neurological, integument and muscular body systems. In one embodiment of the invention, the shaped medical devices are used in the treatment of cardiovascular, neurological, kidney, or liver disease.

Crosslinkable Polymers

The shaped medical devices of this invention are fabricated from crosslinkable polymers which may be anionic or cationic in nature and include, but are not limited to, carboxylic, sulfate, hydroxy and amine-functionalized polymers, normally referred to as hydrogels after being crosslinked. The term "hydrogel" as defined herein is a crosslinked, water-insoluble, water-containing (e.g., hydrophilic) polymeric material.

Suitable crosslinkable polymers which may be used in the present invention include, but are not limited to, one or a mixture of polymers selected from the group consisting of polyhydroxy ethyl methacrylate, polyvinyl alcohol, polyacrylamide, poly (N-vinyl pyrolidone), polyethylene oxide, hydrolysed polyacrylonitrile, polyacrylic acid, polymethacrylic acid, polyethylene amine, polysaccharides (e.g., alginic acid, pectinic acid, carboxy methyl cellulose, hyaluronic acid, heparin, heparin sulfate, chitosan, carboxymethyl chitosan, chitin, pullulan, gellan, xanthan, carboxymethyl starch, carboxymethyl dextran, chondroitin sulfate, cationic guar, cationic starch, as well as salts and esters thereof). Polymers listed above which are not ionically crosslinkable are used in blends with polymers which are ionically crosslinkable.

The most preferred polymers include one or a mixture of alginic acid, pectinic acid, carboxymethyl cellulose, hyaluronic acid, chitosan, polyvinyl alcohol and salts and esters thereof. Preferred anionic polymers are alginic or pectinic acid; preferred cationic polymers include chitosan, cationic guar, cationic starch, and polyethylene amine.

Other preferred polymers include esters of alginic, pectinic or hyaluronic acid, and $C_2$ to $C_4$ polyalkylene glycols (e.g., propylene glycol), as well as blends containing 1 to 99 weight percent (wt %) of alginic, pectinic or hyaluronic acid with 99 to 1 wt % polyacrylic acid, polymethacrylic acid or polyvinyl alcohol. Preferred blends comprise alginic acid and polyvinyl alcohol.

Radiopaque fillers or other filler material can be blended into the crosslinkable polymer to enhance the radiopacity or other properties of the shaped medical device. Suitable radiopaque fillers include, but are not limited to, bismuth sub-carbonate, barium sulfate, bismuth oxychloride, tungsten, bismuth trioxide, tantalum, and the like. Other additives may be incorporated into the crosslinkable polymer including, but not limited to, additives for medical treatment, such as antiseptics, antibiotics, anticoagulants, contraceptives, nucleic acids [e.g., DNA (including genes, cDNAs and vectors), RNA, antisense molecules, ribozymes, PNA molecules], proteins (e.g., ligands, receptors, growth factors, cytokines, vascularizing agents, anti-vascularizing agents, antibodies, and the like), or medicines. In a further embodiment of the invention, additives may be added to only a portion of a medical device. For example, the shaped medical device may be provided in the form of a sheet containing an additive which is used to coat another medical device which does not contain an additive. The other medical device may comprise a dissolvable polymer, a nondissolvable polymer, or a combination of both types of polymers. Additives for mechanical property adjustment may also be provided. In one embodiment of the invention, suture materials or other non-dissolvable materials, may be incorporated into a least a segment of the crosslinkable polymer to provide additional mechanical strength in that segment of the polymer.

Ionic Crosslinking

The crosslinkable polymers according to the present invention may be crosslinked using either non-ionic (e.g., covalent) or ionic crosslinking. Ions used to ionically crosslink the polymers are polyions and may be anions or cations depending on whether the polymer is cationically or anionically crosslinkable. Appropriate crosslinking cations include, but are not limited to, alkaline earth metals, such as calcium, magnesium, barium, strontium, and beryllium ions; transition metals, such as iron, manganese, copper, cobalt, zinc, and silver ions; other metallic elements, such as boron, aluminum, lead, and bismuth ions; and polyamonium ions, such as $^+H_3N-(CH_2)_n-NH_3^+$ or $^+H_3N-(CH_2)_n-CH((CH_2)_m-NH_3^+)((CH_2)_p-NH_3^+)$ where n is an integer ranging from 1 to 8, and m and p are integers ranging from 0 to 8 ions. Anions are derived from polybasic organic or inorganic acids. Appropriate crosslinking anions include, but not limited to, phosphate, sulfate, citrate, borate, succinate, maleate, adipate and oxalate ions. Preferred crosslinking cations are calcium, iron, and barium ions. The most preferred crosslinking cations are calcium and barium ions. The most preferred crosslinking anion is phosphate. Crosslinking may be carried out by contacting the polymers with an aqueous solution containing dissolved ions.

Non-Ionic Crosslinking

In one embodiment of the invention, the crosslinkable polymers forming the shaped medical devices of this invention are crosslinked by non-ionic crosslinking mechanisms to produce a device having a higher crosslink density and improved mechanical properties, i.e., improved stiffness, modulus, yield stress and strength. This may be accomplished by additionally subjecting the ionically crosslinkable polymer to non-ionic crosslinking mechanisms such as high energy radiation (gamma rays) or treatment with a chemical crosslinking agent which reacts with groups present in the polymer such that covalent bonds are formed connecting different portions of the polymer or between polymer strands to form a web. Another non-ionic crosslinking mechanism useful with respect to some classes of hydrogel polymers is physical crosslinking. This is accomplished by crystal formation or similar association of polymer blocks such that the polymer molecules are physically tied together and prevented from complete dissolution. Non-ionic crosslinking may be carried out prior to, subsequent to, or concurrently with, ionic crosslinking.

The most preferred method for non-ionic crosslinking is contact of an ionically crosslinkable polymer with a chemical crosslinking agent because the degree of crosslinking can be more readily controlled, mainly as a function of the concentration of the crosslinking agent in the reaction medium. Suitable crosslinking agents are polyfunctional compounds preferably having at least two functional groups reactive with one or more functional groups present in the polymer. Preferably the crosslinking agent contains one or more of carboxyl, hydroxy, epoxy, halogen, amino functional groups, or hydrogen unsaturated groups, which are capable of undergoing facile nucleophilic or condensation reactions at temperatures up to about 100° C. with groups present along the polymer backbone or in the polymer structure. Suitable crosslinking reagents include polycarboxylic acids or anhydrides; polyamines; epihalohydrins; diepoxides; dialdehydes; diols; carboxylic acid halides, ketenes and like compounds. A particularly preferred crosslinking agent is glutaraldehyde.

In one embodiment of the invention, crosslinkable polymers are provided which possess pendant organic acid functional groups which are covalently crosslinkable with polyfunctional crosslinking agents. In this embodiment of the invention, the covalent bonds between the crosslinking agents and the hydrophilic polymers are susceptible to hydrolysis in the body, releasing water-soluble components. For purposes of the present invention, the term "organic acid functional group" includes any functional group which contains an acidic, ionizable hydrogen. Examples of such functional groups include free carboxylic, free sulfuric, and free phosphoric acid groups, their metal salts and combinations thereof. Such metal salts include, for example, (1) alkali metal salts, such as lithium, sodium and potassium salts, (2) alkaline earth metal salts, such as calcium or magnesium salts, and (3) quaternary amine salts of such acid groups, particularly quaternary ammonium salts.

The preferred covalent crosslinking agents are ones that can form relatively weak covalent crosslinking bonds, so that these bonds can be "unzipped" or "de-crosslinked" within the body after a desired length of time. For example, polymers comprising covalent bonds that are easily hydrolysable at temperature and pH conditions inside the body are desirable. In the present invention, preferred polyfunctional covalent crosslinking agents include polyfunctional aziridines, polyfunctional carbodiimides, polyisocyanate, glutaraldehyde or other polyfunctional crosslinkers wherein the functional groups are capable of reacting with the organic acid groups, or any activated forms thereof.

The term polyfunctional carbodiimide as used herein includes compounds having more than one carbodiimide group corresponding to the general formula (I):

$$R-(N=C=N-R')_n- \quad (1)$$

wherein n is an integer superior or equal to 2, and preferably ranging from 2 to 8, and wherein R and R' are the same or different and are linear, branched, or cyclic alkyl, substituted alkyl, alkenyl, aryl, aralkyl, alkylaryl, or substituted aryl groups containing 1–18 carbon atoms wherein 1 to 3 carbon atoms may be substituted by an oxygen, an acetate, or sulfur atom or group. More specifically the carbodiimides which are useful in this invention are those in which R and R' are methyl, ethyl, propyl, butyl, amyl, hexyl, heptyl, octyl, nonyl, decyl, undecyl, dodecyl, cyclopentyl, cyclohexyl, fluoroalkyl, chloroalkyl, or bromoalkyl groups; allyl, methylallyl, aralkyl such as benzyl, phenyl ethyl, methyl benzyl, trimethyl benzyl, trityl, or the corresponding alkyl substituted naphthyl groups in which said alkyl groups contain an aggregate of from 1 to 18 carbon atoms; alkylaryl groups such as toluyl, xylyl, methyl naphthyl, or other alkyl substituted phenyl and naphthyl groups in which the alkyl group contains 1 to 18 carbon atoms; nuclear halogenated aryl groups such as flurophenyl, chlorophenyl, bromophenyl, iodophenyl and nitrophenyl, cyanophenyl, alkoxyphenyl said alkoxy group containing 1 to 18 carbon atoms; or di-alkylaminoaryl said alkyl groups on said amino group containing a total of from 1 to 18 carbon atoms and the aryl group can be phenyl, halogenated phenyl, nitrophenyl, cyanophenyl, alkoxyphenyl, naphthyl, or fluoronaphthyl. The R and R' can be the same or different hydrocarbons or substituted hydrocarbon groups as defined as above.

The preferred carbodiimides for the purpose of this invention are polyfunctional polycarbodiimides derived from the reaction of mono-, di-, and tri-cycloaliphatic or saturated aliphatic isocyanates, wherein the cycloaliphatic moieties contain from 5 to about 7 carbons, and can be substituted with alkyl having 1 to about 6 carbons, and oxygen and the saturated aliphatic moieties contain from 1 to about 18 carbons.

The reactivity of the carbodiimides with the organic acids in the crosslinkable polymer is dependent upon the nature of R and R' in formula (I). When a rapid crosslinking is desired the most effective carbodiimides are those in which R and R' are alkyl groups. When a slow crosslinking rate is desired, the most effective carbodiimides are those in which R and R' are aryl.

The term "polyfunctional aziridine crosslinking agent" as defined herein means a crosslinking agent with at least two nitrogen atoms. These crosslinking agents have one of the nitrogens in an aziridine ring, while the other is present in a side chain bonded to the aziridine nitrogen. An example of the simplest polyfunctional aziridine crosslinking agents is N-(aminoethyl) aziridine. Those polyfunctional aziridines having about three to about five nitrogen atoms per molecule of crosslinking agent are preferable. Examples from this class of crosslinking agents include, but are not limited to, N-aminoethyl-N-aziridylethylamine, N,N-bis-2-aminopropyl-N-aziridylethylamine, and N-3,6,9-triazanonylaziridine.

In additional embodiments of the invention, other crosslinking agents are used which include, but are not limited to, commercially available preparations of the trifunctional aziridine sold by Zeneca Resins under the trade name NeoCryl CX 100 agent having equivalent weight of 156 atomic mass units, and those preparations sold by EIT Industries under the trade name XAMA-7. For example, a commercially available polyfunctional carbodiimide which is also useful in the present invention is Ucarlink XL-29SE, sold by Union Carbide.

Preferably, the covalent crosslinking agent has more than two functional groups per molecule. Furthermore, the present invention also encompasses covalent crosslinking using a combination of different polyfunctional crosslinking agents.

Among the polyfunctional aziridines useful in the present invention are the trifunctional aziridines of the following formula (II):

Below, is an illustration of the crosslinking reactions between the hydrophilic polymer and the crosslinking agents of formula (III) (i.e., aziridine).

wherein R1 is a linear, branched, or cyclic alkyl, substituted alkyl, alkenyl, aryl, aralkyl, alkylaryl, and substituted aryl groups containing 1–18 carbon atoms wherein 1 to 3 carbon atoms may be substituted by an oxygen, an acetate, or a sulfur atom or group. More specifically the aziridines which are useful in this invention are those in which R1 is methyl, ethyl, propyl, butyl, amyl, hexyl, heptyl, octyl, nonyl, decyl, undecyl, dodecyl, cyclopentyl, cyclohexyl, fluoroalkyl, chloroalkyl, or bromoalkyl group; allyl, methylallyl, aralkyl such as benzyl, phenyl ethyl, methyl benzyl, trimethyl benzyl, trityl, or the corresponding alkyl substituted naphthyl in which said alkyl groups contain an aggregate of from 1 to 18 carbon atoms; alkylaryl such as toluyl xylyl, methyl naphthyl, or other alkyl substituted phenyl and naphthyl groups in which the alkyl groups contains 1 to 18 carbon atoms; nuclear halogenated aryl groups such as flurophenyl, chlorophenyl, bromophenyl, iodophenyl or nitrophenyl; cyanophenyl, alkoxyphenyl said alkoxy group containing 1 to 18 carbon atoms; or di-alkylaminoaryl said alkyl groups on said amino group containing a total of from 1 to 18 carbon atoms and the aryl group can be phenyl, halogenated phenyl, nitrophenyl, cyanophenyl, alkoxyphenyl, naphthyl, or fluoronaphthyl.

An example of a reaction for carbodiimide of general formula (III) wherein R and R' are as defined above, with organic-acid-containing hydrophilic polymer (P—COOH) is shown in the following scheme:

material are polymers of glycolic acid, ε-caprolactone, lactic acid, or copolymers thereof, and the like.

Figure 3:
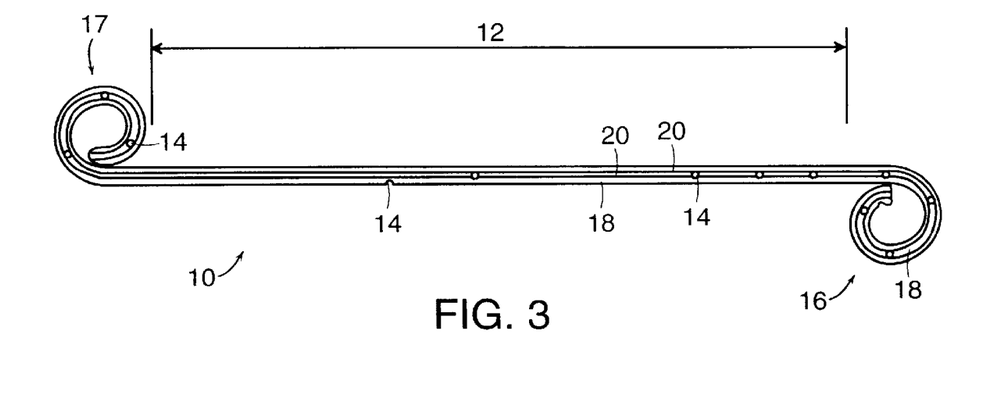
FIG. 3 is an illustration of a stent according to one embodiment of the present invention featuring alternating stripes of varying polymeric materials along its length.
Figure 4A:
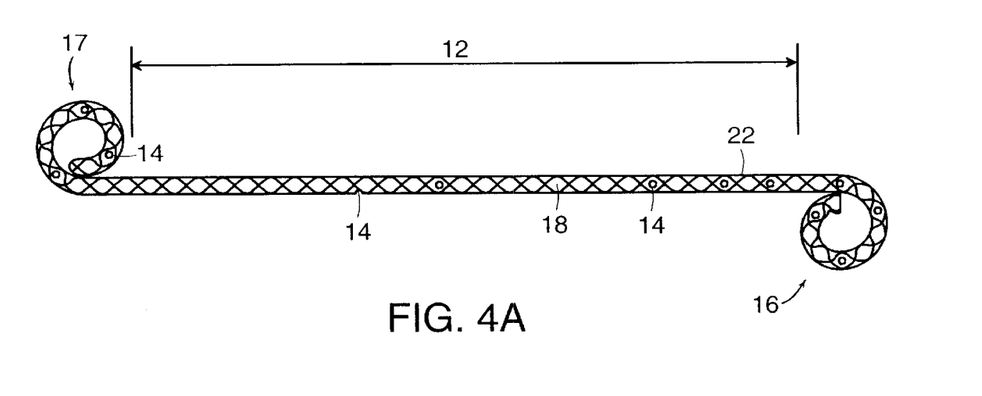
FIGS. 4A–4B are illustrations of stents according to embodiments of the invention featuring suture material in the form of a mesh embedded in, or coextruded with, the hydrogel.
Figure 4B:
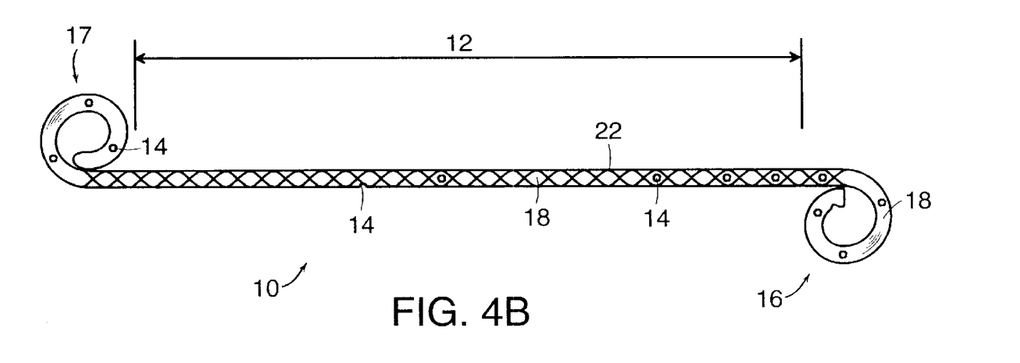

In further embodiments of the invention, short or thin portions of non-dissolvable polymer, such as strings (shown in FIG. 3) or meshes (as shown in FIGS. 4A and 4B), are used because they generally are more easily eliminated from the body without creating obstructions. In another embodiment of the invention, a shaped medical device is provided which comprises a relatively straight section (e.g., the tubular body of a stent) which is reinforced with a biodegradable suture or braid, and a curved portion (e.g., the pigtail end of a stent) which is not reinforced. The curved portion anchors the shaped medical device at a particular location within the body. In this embodiment, the non-reinforced curved portion of the device weakens or degrades first. This allows the relatively straight section of the device to migrate to a point of egress (e.g., in the case of a ureteral stent, to the bladder).

Alternatively, the shaped medical device according to the present invention includes a weak point, or break point, in a relatively straight section of the device proximal to a curved section of the device. As defined herein "proximal" means near enough to the curved section such that when the device is broken at the break point, less than 50% of the relatively straight section remains associated with the curved section. In one embodiment of the invention, the break point is adjacent to the curved section.

In a further embodiment of the invention, the shaped medical device is a stent having a relatively straight tubular body and at least one pigtail end having a weak point or break point proximal to a pigtail end. When the stent is a ureteral stent, breaking the stent at the break point allows for migration of most of the stent into the bladder, leaving a small section in the kidney to dissolve or migrate at a later time. In this embodiment, the pigtail end is not required to dissolve for the majority of the stent to migrate.

Controlled Dissolution

Displacement of crosslinking ions from the shaped medical device can be accomplished by flowing a solution containing a stripping agent around and/or through the medical device in vivo. The stripping agent serves to displace, sequester, or bind, the crosslinking ions present in the ionically crosslinked polymer, thereby removing the ionic crosslinks. Stripping agents according to the present invention are polyions capable of forming stable ionic bonds with the cations or anions disclosed above. The choice of The concentration of the covalent crosslinking agent in the shaped medical device in this embodiment is in the range from about 0.2% to about 40% by weight solids content. In another embodiment of the invention, the concentration of covalent crosslinking agent is from about 0.5% to about 20% by weight solids content of the shaped medical device.

Heterogeneous Polymers

In one embodiment of the invention, the crosslinkable polymer is also combined with short segments of non-dissolvable, non-disintegratable polymer(s), or biodegradable suture material to increase the versatility of the shaped medical device. The segments may be spaced at regular or irregular intervals. Such non-dissolvable polymer(s) or biodegradable suture material(s) provide added strength to a device undergoing dissolution and/or disintegration. Suitable non-dissolvable polymers include, but are not limited to, silicones, and the like. Suitable biodegradable suture any particular stripping agent will depend on whether the ion to be displaced is an anion or a cation. If the crosslinking agent is a cation, then the stripping agent will be a polyanion, while if the crosslinking agent is an anion, the stripping agent will be a polycation. Suitable stripping agents include, but are not limited to, organic acids and their salts or esters, phosphoric acid and salts or esters thereof, sulfate salts and alkali metal or ammonium salts.

Examples of stripping agents include, but are not limited to, ethylene diamine tetraacetic acid, ethylene diamine tetraacetate, citric acid and its salts, organic phosphates, such as cellulose phosphate, inorganic phosphates, such as, pentasodium tripolyphosphate, mono and dibasic potassium phosphate, sodium pyrophosphate, phosphoric acid, trisodium carboxymethyloxysuccinate, nitrilotriacetic acid, maleic acid, oxalate, polyacrylic acid, as well as sodium, potassium, lithium, calcium and magnesium ions. Preferred agents are citrate, inorganic phosphates, and sodium, potassium and magnesium ions. The most preferred agents are inorganic phosphates and magnesium ions.

Specific methods for introduction of the stripping agent include introduction through the diet of the patient or through parenteral feeding, introduction of a solution directly onto the shaped medical device, such as by insertion of a catheter which injects the agent within the device, or through an enema.

In one embodiment of the invention, the shaped medical device is an implanted calcium alginate ureteral stent which is strippable by phosphate anions. In this embodiment, the device is stripped by including in the patient's diet, materials which bind phosphate (e.g., calcium salts) to lower the content of $PO_4^{-3}$ present in the urine (normally up to about 0.1%.). Achievement of levels of phosphate in the urine of from 0.2 to 0.3% will result in the in vivo stripping of the calcium ions from the calcium alginate stent. Lower levels of phosphate in the urine will also result in a more gradual stripping of the calcium ions, but higher levels are preferred for rapid stripping of the calcium.

Another advantage of the invention is that the stripping process may be reversed to re-stiffen the shaped medical device which facilitates surgical removal of the device from the body. This may be accomplished by flowing a source of crosslinking ions through and/or around the shaped medical device to ionically re-crosslink the implant, essentially the reverse of the stripping process described above. Dietary modifications can also be used to re-crosslink the shaped medical device in vivo, e.g., by eliminating phosphate binders (endogenous or exogenously added) from the diet and adding foods or other dietary supplements which provide or generate phosphate ions in the body.

The present invention also provides several means of controlling or slowing the dissolution rate of the ionically crosslinked material upon exposure to a stripping agent. In general, a polymer that has a higher ionic crosslinking content will dissolve more slowly than a polymer that has a lower ionic crosslinking content. By modifying the amount of ionic crosslinking in different portions of the shaped medical device, it is possible to design devices which dissolve in at non-uniform rates along different portions of the device. In one embodiment of the invention, a stent is provided which has pigtail ends with a relatively low ionic crosslinking content compared to the tubular body of the stent. In this embodiment of the invention, the pigtail ends dissolve faster than the tubular body. When the stent is a ureteral stent placed in the kidney, the dissolution of a pigtail end located in the kidney permits migration of the stent within the ureter and into the bladder. In a further embodiment of the invention, a similar result is achieved by modifying the thickness of the walls of the shaped medical device, e.g., thinner walls will dissolve faster than thicker walls. In one embodiment of the invention, a stent is provided having pigtail ends with thinner walls than its tubular body.

In still another embodiment of the invention, a medical device in the form of a sheet may be provided as a coating for an underlying medical device. In one embodiment, the composition of the sheet is optimized to allow the sheet to dissolve more quickly than the underlying medical device. In this embodiment, when the sheet-shaped medical device comprises an additive (e.g., a medicine or drug), the sheet will dissolve first, delivering a desired amount of additive to a target site, while the underlying device maintains its structural integrity at the target site. In one embodiment, where the underlying device is a stent and is placed in a blood vessel, the sheet portion of the device may be used to deliver an anti blood vessel occluding agent, while the stent portion of the device acts as a prosthesis to maintain the opening of the blood vessel. In some embodiments of the invention, the underlying medical device may be completely non-dissolvable.

Yet another way of achieving varied dissolution rates between differing sections of the shaped medical device is to use the difference in the affinity of various crosslinking ions. The greater affinity the crosslinking ion has, the slower the rate of dissolution of the ionically crosslinked polymer. Cationic crosslinking ions have the following affinity order (from the lowest to the highest):

A similar scale may be established for anionic crosslinking ions. The greater the basicity (or higher $pK_a$ value) of the anion the slower the rate of dissolution. The $pK_a$ values of acids and bases are well known in the art.

Thus, the rate of dissolution of a shaped medical device (e.g., a stent) may be controlled by selecting an ion that has a greater affinity (or basicity) to slow the dissolution process. In one embodiment of the invention, to prepare a stent that has faster dissolving pigtail ends, the stent is crosslinked in the pigtail end with a low affinity (or basicity) ion (such as $Mg^{2+}$ or $Ca^{2+}$ for anionic polymers), and with a high affinity (or basicity) ion (such as $Ba^{2+}$ or $Zn^{2+}$) in the elongate tubular portion of the stent.

Alternatively, the shaped medical device (e.g., stent) may contain both types of crosslinking cations, i.e., low and high affinity, such as barium and calcium ions. In this embodiment, the cations are provided in differing concentrations in different sections of the device. For example, the ends of the shaped medical device (e.g., the pigtail portions, in the case of a stent) would have low concentrations of high affinity cations (e.g., $Ba^{2+}$) and high concentrations of low affinity cations (e.g., $Ca^{2+}$), and while the body of the device (e.g., the tubular body in the case of a stent) would have high concentrations of high affinity cations (e.g., $Ba^{2+}$) and low concentrations of low affinity cations (e.g., $Ca^{2+}$).

Ureteral stents manufactured according to the present invention substantially reduce the risk of hydronephrosis of the kidney which results from obstruction of the ureter by stent fragments. An added benefit of the stents according to the present invention is increased patient comfort, since the stents are made of a temporary material which will resorb, biodegrade, disintegrate, or erode, after placement in vivo, eventually becoming expelled through the urethra upon urination. In one embodiment of the invention, a ureteral stent is provided which comprises an initially high durometer (e.g., about 50–100 Shore A) for ease of placement in the body which reduces to a lower durometer (e.g., about 20–50 Shore A) for enhanced patient comfort while it functions as a stent. In a further embodiment of the invention, at least one end of the stent comprises a coiled end. In this embodiment of the invention, at the end of the stent's service life, the coiled end residing in the kidney continues to soften and weaken, ultimately migrating in a single intact piece through the ureter and into the bladder. Once in the bladder, the material continues to break down into smaller pieces either by chemical breakdown or physical agitation from an expanding or contracting bladder. In this part of the body, fragments are harmlessly expelled.

In one embodiment, a ureteral stent is produced which is composed of an alginate material and reversibly crosslinked with 19% by weight of barium and 0.17% by weight of calcium. In this embodiment the stent has a pigtail or coil on either end to prevent migration after initial placement. The stent also contains a radiopacifier (e.g., bismuth subcarbonate or barium sulfate) to make it visible under fluoroscopy, whether fully intact or in fragments. The stent has an initial durometer of about Shore 60A, but softens to about Shore 30A after a short period of time. This softer durometer provides for increased patient comfort. The pigtail strength maintains a minimum of 20 grams for at least 48 hours after insertion into the body. From 2 days to 14 days, the pigtail's strength diminishes to a point that allows the stent to migrate to a point of egress (e.g., the bladder) prior to fragmenting. After migrating, the stent continues to break into smaller pieces or erode to a smaller diameter so that it can be easily and readily expelled.

To produce a stent that has a faster rate of dissolution in the pigtail ends, the following process may be applied. Sodium alginate is first extruded as a hollow tube into a bath containing barium ions. The ends of the stent are then consecutively dipped into a bath containing a sequestant for barium ions, such as ethylene diamine tetraacetic acid or phosphate. The ends are then coiled to form the pigtail and dipped into a bath containing calcium ions. Crosslinking of the ends with calcium also set their coiled shape.

Dual Crosslinked Polymers

In other embodiments of the invention, dual crosslinked shaped medical devices are provided, i.e., containing both non-ionic and ionic crosslinks. In these embodiments, the ionic crosslinks can be easily and selectively displaced in vivo after implantation of the device in the body while the non-ionic crosslinks are not significantly removed. Consequently, the shaped device swells and softens in vivo, enhancing patient comfort, while retaining its original non-ionically crosslinked shape configuration to a large degree.

The covalent bonds in the dual crosslinked shaped medical devices make the device water-insoluble. The device will soften upon removal of the ionic crosslinking agents or hydration and will be able to migrate in the body. However, the covalent bonds are also susceptible to hydrolysis within the body and thus the devices will degrade over time.

In certain embodiments of the invention, the dual crosslinked shaped medical devices comprise covalent and ionic crosslinks throughout the device in the following ratio ranges: (1) covalent crosslinking occupies 0.1%–100% of the available crosslinking sites of the hydrophilic polymer; and (2) ionic crosslinking occupies 0%–99.9% of all available crosslinking sites of the hydrophilic polymer. The crosslinking sites are the sites on the hydrophilic polymer where a pendent organic acid group is available to react with a crosslinking agent.

In those embodiments, the dissolution and disintegration of the shaped medical device occurs simultaneously throughout the device, but at a different rate for each type of crosslinking. In general, dissolution (i.e., removal of the ionic crosslinks) will occur at a faster rate than disintegration (i.e., hydrolysis of the covalent crosslinks). Thus, the shaped medical devices first soften upon the loss of ionic crosslinks while maintaining the overall shape and structural cohesion provided by the covalent crosslinks. Such softened shaped medical devices may provide for easy and painless removal of the device by natural migration through body vessels. In the case of a temporary ureteral stent, for example, the softened stent would migrate out of the ureter and kidney to the bladder where it would slowly disintegrate and be eliminated as water-soluble components or by-products are released.

Forming Medical Devices Having Desired Shapes

The crosslinked shaped medical devices according to the invention are shaped by extrusion, molding, compression of the polymers, or other means, before the polymer is covalently or ionically crosslinked. The shaped medical devices in final form are crosslinked to maintain their shape. One process for manufacturing a shaped medical device according to the present invention comprises introducing a solution comprising ionically crosslinkable polymer through a die to form a tube while simultaneously pumping a solution comprising crosslinking ion through the die.

Linear device or pre-device configurations such as fibers, rods, tubes or ribbons can be manufactured in accordance with the present invention by using a spinning device in which an aqueous solution of an ionically crosslinkable matrix polymer is forced through a shaping die into a crosslinking bath containing the crosslinking ions. The product after crosslinking is typically described as a hydrogel. The hydrogel may be used as made, or further given a three-dimensional shape through treatment in a crosslinking solution after being forced into the desired shape. After equilibration, the hydrogel will retain the new three-dimensional shape. The device may be used in its hydrogel form or in a dehydrated form. During dehydration, the three-dimensional shape is retained.

In one embodiment of the invention, the shaped medical device is shaped by wet spinning to form a tube. In a further embodiment of the invention, the shaped medical device is formed into a tubular shape by molding a crosslinkable polymer in a one- or two-part reaction injection molding system. As defined herein, the term "tube" or "tubular shape" refers to a generally cylindrical device having a substantially uniform circular cross-section throughout the device and to a device having cross-sections of varying shapes and sizes, so long as the device has a hollow passageway with at least one opening through which fluid may enter and at least one opening through which fluid may leave.

The shaped medical device may be stored wet or dry. In one embodiment, the medical device is stored in an aqueous solution or buffer or (e.g. deionized water, or water containing hygroscopic agents, such as glycerol, sorbitol, sucrose, and the like). In another embodiment of the invention, the shaped medical device is dried prior to storage.

To produce shaped medical devices having a homogenous distribution of ionic and non-ionic crosslinks throughout the device, the crosslinkable polymer shaped into the desired implant is dipped consecutively into two baths, each bath containing one type of crosslinking agent. For example, the entirety of the crosslinkable polymer may be dipped into a first bath containing a solution of crosslinking cations to ionically crosslink a portion of the available crosslinking sites of the polymer; then, the least partially ionically crosslinked polymer is dipped into a second bath containing a solution of covalent crosslinking agent to covalently crosslink a portion, or all of, the remaining available crosslinking sites of the hydrophilic polymer. The extent of each type of crosslinking may be varied by varying the length of time of exposure of the shaped medical device to each type of crosslinking agent or, alternatively, by masking portions of the device. In one embodiment of the invention, prior to molding the crosslinkable polymer into a desired conformation, the crosslinkable polymer and crosslinking agents may be cast into a sheet or first to test the mechanical properties of the crosslinked polymer. When a crosslinked polymer having satisfactory properties is obtained, the same concentration of crosslinkable polymer and crosslinking agents may used to form a shaped medical device having a more complex shape, such as a tube.

In one embodiment of the invention, a biliary or ureteral stent is fabricated which has improved modulus (stiffness) properties due to dual crosslinking. Such stents are robust enough and sufficiently resistant to buckling to allow them to be readily inserted into the appropriate part of the body with an endoscope. Once inserted, the ionic crosslinks present in the stents can be selectively, at least partially stripped, either directly by the physician, by dietary means, or by means of exposure to natural body fluids such as bile or urine. As the ionic crosslinks are removed, the modulus of the stents are lowered and the stents soften and swell in body fluids, resulting in a more comfortable and conformable element and a larger lumen through which body fluids may flow. An enlarged lumen is preferred in tubular shaped medical devices to allow higher flow rates, to enhance the anchoring of the device to the body, and to decrease the likelihood of occlusion during use.

To form such a stent, sodium alginate is extruded into a stent shape by precipitating alginate tubing into a calcium bath. The stent is placed on a pre-shaped fixture with pigtail ends and calcium ions are stripped by dipping into a bath containing stripping agents. The alginate tubing is then covalently crosslinked with a polyfunctional crosslinking agent.

The stent may be crosslinked to various degrees along the length of the stent to optimize the function of the shaped medical device. For example, in designing a ureteral stent, the pigtails will be formed using sufficient covalent crosslinking to prevent their breaking in the kidney; however, they will also be designed to become soft after a certain time so that as they lose their strength they can be straightened and migrate out of the kidney.

In another embodiment, a ureteral stent is made of different polymers (e.g., either entirely hydrophilic or at least partially hydrophilic) along the length of the stent. In this embodiment, the pigtail ends are made of dissolvable material and the tubular body is made of a combination of semi-dissolvable and non-dissolvable materials. If non-dissolvable material is used for any part of the stent, the material should be short and flexible enough to migrate inside the urinary track (e.g., a piece of suture material). A long stent can be made by joining one or more short non-dissolvable pieces to a dissolvable portion of the stent. The joining material in this embodiment should be dissolvable.

In further embodiments of the invention, several batches of hydrophilic polymer are prepared. In one embodiment, batch 1 comprises a mixture of hydrophilic polymers with a covalent crosslinking agent; batch 2 comprises a mixture of hydrophilic polymers with a ionic crosslinking agent; and batch 3 consists essentially of the hydrophilic polymer by itself. In additional embodiments, shaped medical devices having various sections made of differing types of crosslinking are prepared by molding or extruding the implant with material selected alternatively from any one of batches 1, 2, and 3. The resulting extruded or molded implant may be further treated by heat, for example, to set the covalent crosslinking process, or further exposed to ionic crosslinking agents.

In other embodiments, dual crosslinked shaped medical devices are made of discrete segments of non-ionically and ionically crosslinked hydrogel polymer. In these embodiments, different portions of the device dissolve or disintegrate at different rates, leading to the breakdown of the shaped medical device in small chunks or segments that can migrate through the body vessels without causing undesirable obstructions of these vessels.

To produce implants having a plurality of alternating segments of both non-ionic and ionic crosslinks, the segments of the implant desired to be ionically crosslinked are dipped into a bath containing an ionic crosslinking agent. The remaining segments desired to be covalently crosslinked are then dipped into a bath containing a covalent crosslinking agent. Such a process is particularly suitable for the preparation of ureteral stents. In this embodiment, the pigtail ends of the stent are ionically crosslinked and the tubular body of the stent is covalently crosslinked.

Selective Shaping of Dual Crosslinked Polymers

In one embodiment of the invention, selective de-crosslinking and re-crosslinking is used to change the shape of the medical device, in vitro or in vivo. In in vivo applications, this allows the device to be placed in the body in a shape that facilitates insertion and to be retained in the body in a shape that facilitates anchoring and patient comfort.

In one embodiment of the invention, a secondary shape is imparted to the medical device prior to implantation in the body. This is accomplished by deforming the primary shape of a device which is crosslinked at least non-ionically, setting the device in the deformed shape by ionic crosslinking, and implanting the device in the body in the deformed shape. Stripping the ions in vivo as described above will cause the device to revert in vivo to its primary non-ionically crosslinked shape. In accordance with one aspect of this invention, an ionically crosslinkable polymer is formed into a primary shape and subjected to non-ionic crosslinking conditions to form a non-ionically crosslinked hydrogel having this primary shape. Non-ionic crosslinking can be carried out by the methods described above, and is preferably carried out by extruding the polymer into a bath containing a sufficient amount of one or more of the non-ionic crosslinking agents to form a shape-retaining hydrogel. Next, a secondary shape is imparted to the non-ionically crosslinked hydrogel and the hydrogel is then subjected to ionic crosslinking conditions to ionically crosslink the hydrogel while retaining this secondary shape.

In another aspect of the invention, an ionically crosslinkable polymer is formed into a primary shape and subjected to both non-ionic and ionic crosslinking conditions to form a crosslinked polymer having the primary shape and containing both ionic and non-ionic crosslinks. In this embodiment, an ionically and non-ionically crosslinked shaped polymer is prepared as above. Then, the shaped polymer is selectively stripped ex vivo of at least a portion or essentially all of the crosslinking ions; the shaped polymer is then conformed to a secondary shape, e.g., bent around a wire, stretched, compressed, or the like. The shaped polymer is subsequently ionically re-crosslinked while retained in the secondary shape. Release of the crosslinking ions in vivo will cause the implanted device to revert substantially to the original primary, non-ionically crosslinked shape. The stripping step described above can occur immediately prior to, or subsequent to the secondary shaping step, but preferably subsequent to the secondary shaping step and prior to the ionic re-crosslinking step.

This embodiment is particularly useful where the shaped medical device is of hollow, tubular configuration, such as a stent. Where the stent is both ionically and non-ionically crosslinked, it may be selectively stripped of crosslinking ions. In one embodiment, the stent is stretched to form a narrower stent which facilitates insertion into the body, ionically crosslinked or re-crosslinked in the stretched state to fix the stent in the stretched state, implanted in the body and then re-stripped in vivo of the ionic crosslinks to produce a softer shaped device having a wider lumen. Other stent shapes such as pigtail ends, flaps, curves, and the like can be developed in vivo by subjecting devices having these primary initial shapes to the process described above, i.e., deforming the primary shape ex vivo and reforming the primary shape in vivo.

The stripping step described above is preferably accomplished by dipping or spraying the crosslinked shaped device with an aqueous electrolyte solution for an appropriate time to selectively strip the crosslinking ions from the device. Preferred electrolytes for ex vivo stripping are chlorides of monovalent cations such as sodium, potassium or lithium chloride, as well as other stripping salts described above. The concentration of the electrolyte salt in the solution may range from about 1 weight percent (wt %) up to the solubility limit. The solution may also contain plasticizing ingredients, such as glycerol or sorbitol, to facilitate inter- and intra-polymer chain motion during, and after, secondary shaping. Secondary shaping of the medical device may be done by hand, i.e., using pinning boards or jig pins, or by using shaped presses or molds.

In another embodiment, the device may be ionically crosslinked or re-crosslinked in the secondary shape by contacting the device, while retaining the secondary shape, with an aqueous solution containing the crosslinking ions described above. After crosslinking, the device will essentially retain the secondary shape.

The ionically crosslinked, shaped polymer prepared as above is then subjected to non-ionic crosslinking, e.g., high energy radiation or by contact under appropriate acidic or basic conditions with the appropriate chemical crosslinking agent. Crosslinking is preferably carried out by soaking the polymer in an aqueous solution containing a water soluble crosslinking agent such as glutaraldehyde, ethylene diamine or a lower alkylene glycol. Generally, the concentration of crosslinking agent in solution may range from about 0.25 to about 10 wt %, more preferably from about 0.5 to 5.0 wt %. The degree of non-ionic crosslinking is controlled as a function of the concentration of the crosslinking agent in solution. The level should be selected such that a stiffer, higher modulus shaped medical device is produced which will revert to a soft, stretchy, shape retaining device after removal of the ionic crosslinks. The crosslinking process may also be conducted by first crosslinking the polymer non-ionically, followed by ionic crosslinking, essentially the reverse of the process described above.

Where the ionically crosslinkable polymer composition includes polymers which are partially water soluble, it is preferred to include in the aqueous spinning solution and treatment solutions described above one or more additives which retard the tendency of the solution to dissolve the polymer, i.e., providing non-solvent conditions. Example of such conditions include high salt concentrations, or inclusion in the solution of additives such as borax, boric acid, alkali metal salts and/or a lower alcohol such as methanol.

The various steps may be performed at any suitable temperature, e.g., at room temperature or at temperatures up to about 100° C. Preferably, soaking steps are conducted at room temperature. Moreover, the steps may be performed one immediately after another, or a drying step (e.g., air-drying) may be interposed between one or more steps. Additionally, the shaped medical device may be sterilized after the sequence of secondary-shaping steps.

EXAMPLES

Exemplary hydrogel systems which may be prepared in accordance with this invention are prepared by the following procedures:

Example 1

Alginate Which Has Been Covalently and Tonically Crosslinked.

A solution of sodium alginate is extruded through a tube die into a calcium chloride bath while calcium chloride solution is simultaneously introduced through the lumen of the tube. This ionically crosslinked tube is then covalently crosslinked by treatment with an aqueous solution containing glutaraldehyde. The now covalently and ionically crosslinked gel has a higher crosslink density and therefore higher modulus than a similar tube having only the covalent or only the ionic crosslinks. The tube therefore has higher stiffness and improved resistance to buckling than a tube having the covalent or ionic crosslinks alone. After insertion into the body, exposure of the tube to ions in body fluids will remove the calcium crosslinks, lower the modulus of the gel and therefore reduce the stiffness of the tube, allowing for maximum patient comfort and biocompatibility. Suitable ions which will displace the calcium crosslinking ions include phosphate, sulfate, carbonate, potassium, sodium and ammonium. When implanted the device may be stiffened and strengthened during removal from the body via exposure of the device to an infusion fluid which contains a solution of the crosslinking ions (e.g., calcium).

Example 2

Stent Comprising a Dissolvable Coating

A solution of sodium alginate may be contacted with calcium chloride and cast as a film into a container (e.g., a culture dish or petrie plate), thereby forming a shaped medical device in the form of a sheet. The sheet which may be rolled around another tubular shaped medical device, such as the one disclosed in Example 1, e.g., to form a coating for a stent. Additives (e.g., medicines or drugs) may be provided during casting or shortly before, to be incorporated into the sheet.

Example 3

Polyvinyl Alcohol and Alginate

A blend of polyvinyl alcohol (PVA) and sodium alginate may be dispersed or dissolved in water, extruded into a bath containing calcium ions. The bath additionally contains non-solvent conditions for the polyvinyl alcohol. The polyvinyl alcohol component of the formed article is then covalently crosslinked with an aqueous solution containing glutaraldehyde. The shaped medical device is now ready for insertion and/or implantation. After implantation, the article may be softened and swollen by removal of the ionic crosslinks as above. Removal of the ionic crosslinks may also optionally allow the alginate to fully, or partially dissolve, in the body fluids, leaving behind a less dense, more porous hydrogel. The morphology of the final hydrogel device may be controlled by optimizing of polyvinyl alcohol molecular weight, degree of crosslinking, solvent composition, the molecular weight of the alginate used, the state of the alginate salt (dissolved, particulated, gel), the alginate monomer makeup, as well as the temperature, pressure, mix time, solution age, and rheological factors during manufacture.

Example 4

Shape Memory

The blend of PVA and sodium alginate described in (b) above may be used to make a stent having a shape memory feature to gain increased lumen size after deployment in vivo. A tube is made by extruding the mixture through a tube die into a concentrated calcium chloride bath, optionally containing other salts and boric acid. The tube is then transferred into a bath which contains calcium chloride and a chemical crosslinker (e.g., glutaraldehyde). After allowing the reaction to proceed, the tube will become a covalently crosslinked PVA/calcium alginate system. The tube is immersed in concentrated potassium chloride solution to remove the calcium crosslinks from the alginate while preventing the alginate from dissolving. The tube is then stretched to form a longer length tube having a more narrow lumen. While in this stretched configuration, the tube is immersed into concentrated calcium chloride solution to re-crosslink the alginate. The tube is frozen into the longer length, narrow lumen configuration. Upon insertion into the body, the tube will return to its original shorter length, large lumen configuration, as the calcium is stripped from the alginate. The alginate will eventually dissolve, leaving behind a more porous glutaraldehyde crosslinked PVA tube. Other imposed shapes may be used to accommodate insertion into the body in a compact form, followed by shape change upon displacement of the ionic crosslinks.

Example 5

Propylenezlycol Alginate

Propyleneglycol alginate is covalently crosslinked with ethylene diamine under basic conditions and ionically crosslinked with calcium ions. This covalently and ionically crosslinked material will exhibit higher stiffness than the material crosslinked with covalent linkages only. Removal of the ionic crosslinks will occur in vivo after deployment in body fluid. A stent, catheter, or cannula can be manufactured from this material, implanted while both ionically and covalently crosslinked, the device softens in vivo as the ionic crosslinks are displaced. A shaped device of this construction provides stiffness for implantation and softness for patient comfort.

Example 6

Controlling Stiffness

This example illustrates the preparation of tubing from a mixture of sodium alginate (Protanol LF 10/60 from Pronova Bipolymers A.S., Drammen, Norway) and polyvinylalcohol (PVA). A series of four different formulations were prepared as shown in Table 1.

TABLE 1

| PVA/alginate (wt. rat.) | 15/5 | 20/5 | 15/7.5 | 20/5 |
|---|---|---|---|---|
| Deionized water | 72 g | 67.5 g | 69.7 g | 74.25 g |
| PVA | 13.5 g | 18.0 g | 13.5 g | 19.8 g |

TABLE 1-continued

| Sodium alginate | 4.5 g | 4.5 g | 6.75 g | 4.95 g |
|---|---|---|---|---|
| Bismuth subcarbonate | 9.68 g | 9.77 g | 9.69 g | 9.9 g |

The deionized water was weighed into a 4 oz. jar, while stirring the water, the PVA and sodium alginate were added and mixed until uniform. The jar was capped and heated to 100° C. to dissolve the ingredients. The jar was cooled to 37° C., then the bismuth subcarbonate (radiopaque filler) which had been sifted through a 325 mesh screen was added and the composition was mixed with a jiffy mixer until uniform. The samples were loaded into 30 cc syringes, centrifuged to remove air, then extruded through a tubing die into a coagulant solution. The coagulant solution was made from 100 grams of calcium chloride dehydrate, 30 grams of sodium chloride, 50 grams of boric acid and 820 grams of deionized water. The spun tubing was left in the coagulant solution overnight. Lengths of tubing were then soaked in a glutaraldehyde/coagulant solution mixture to covalently crosslink the sample. Glutaraldehyde levels were tested from 0.5% by weight to 12.5% by weight. The pH was adjusted to 1.5 using 20% HCl solution. After reacting overnight at room temperature, the tubes were examined and then immersed in 0.4% sodium phosphate solution to strip the ionic crosslinks. Results are shown in Table 2.

TABLE 2

| Gutaraldehyde (wt %) | 0.5% | 1.0% | 5.0% | 12.5% |
|---|---|---|---|---|
| 15/5 (PVA/Alginate wt. ratio) | soft, stretchy | slightly stiffer | stiffer, but still soft | stiff, brittle |
| 15/7.5 (PVA/Alginate wt. ratio) | soft, stretchy | slightly stiffer | much stiffer | stiff, brittle |
| 20/5 (PVA/Alginate wt. ratio) | soft, stretchy | slightly stiffer | stiff, brittle | stiff, brittle |

Control samples which were not treated with glutaraldehyde were swollen and broken apart in the phosphate solution.

Example 7

Stent Comprising Alternating Segments of Varying Polymer Types.

Figure 1:
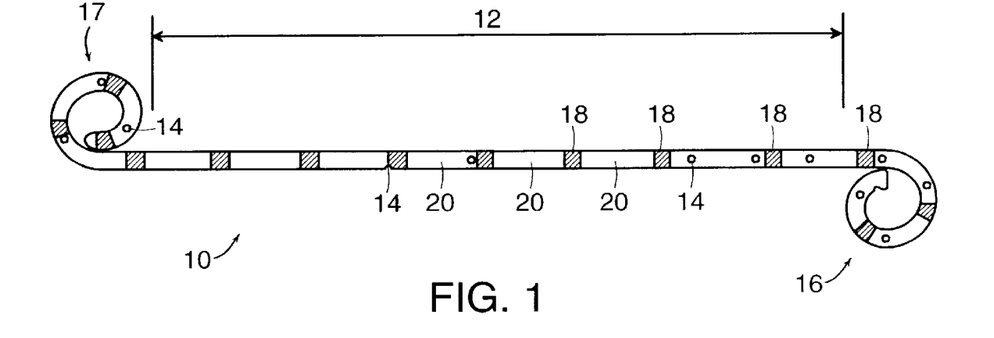
FIG. 1 is an illustration of an embodiment of a shaped medical device according to the present invention featuring alternating short segments of varying polymeric materials.

In FIG. 1, a shaped medical device in the form of a ureteral stent 10 is shown having a pigtail end 16 for positioning into the kidney of a patient, a tubular elongate body 12 for positioning into the ureter, and a second pigtail end 17 for positioning into the bladder. The stent 10 optionally comprises drainage holes 14, throughout the elongate body 12 and the pigtail ends 16 and 17. The stent 10 is molded or extruded from at least two different materials arranged in segments 18 and 20. Each segment may comprise: (1) an entirely ionically crosslinked hydrogel; (2) an entirely non-ionically crosslinked hydrogel; (3) a mixture of non-ionically and ionically crosslinked hydrogels; or (4) non-dissolvable polymer. In the embodiment shown in FIG. 1, segment 18 is a non-dissolvable polymer while segment 20 comprises at least ionic crosslinks. In this embodiment, segments 18 and 20 are alternatively distributed along the length of the stent body at regular intervals. The length of segment 18 is short relative to the length of segment 20 to facilitate removal of the non-dissolvable portion of the stent from the body.

Example 8
Stent Comprising Pigtail End Segments and a Tubular Body Segment.

Figure 2:
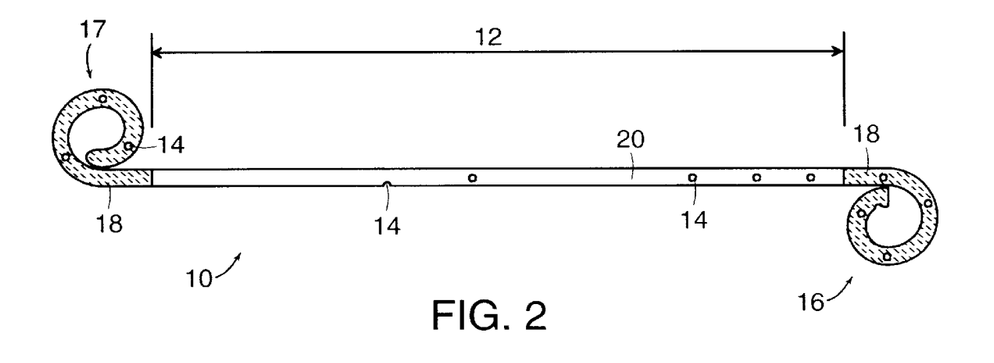
FIG. 2 is an illustration of a stent according to one embodiment of the invention featuring alternating long segments of varying polymeric materials in the pigtail ends and the elongate tubular body of the stent.

FIG. 2 shows a uretral stent 10 having only three segments, a tubular body segment 20 flanked by two pigtail end segments 18. Segments 18 in the pigtail ends 16 and 17 represent a material having a faster rate of dissolution, while segment 20 represents a material having a slower rate of dissolution.

Example 9
Stent Comprising Segments in the Form of Stripes or Strings.

FIG. 3 shows a ureteral stent 10 according to one embodiment of the invention comprising segments 18 and 20 which are in the form of stripes or strings that run parallel to the longitudinal axis of the stent 10 from one pigtail end 16 to the other 17. The thickness of each stripe or string may be varied to achieve the desired strength and desired disintegration rate of the stent 10. In a different embodiment of the invention, the strings themselves comprise suture material or some other non-dissolvable material.

Example 10
Stent Comprising Meshes of Suture Material.

FIG. 4A shows a ureteral stent according to the invention comprising segments 22 which form a mesh of non-dissolvable material or suture material that is co-extruded with the hydrogel and stretches along the length of the stent from one pigtail end 16 to the other 17. FIG. 4B represents an alternative embodiment of the stent where the mesh of non-dissolvable material 22 or suture material is co-extruded with the hydrogel 18 only in the elongate tubular body portion 12.

Having thus described certain embodiments of the present invention, various alterations, modifications, and improvements will be apparent to those skilled in the art. Such variations, modifications, and improvements are intended to be within the spirit and scope of the invention. Accordingly, the foregoing description is by way of example only and is not intended to be limiting.

What is claimed is:

1. A medical device that does not require a surgical procedure for removal comprising a crosslinkable polymer having ionic crosslinks susceptible to dissolution in vivo, the medical device comprising at least two segments that degrade in vivo at different rates.

2. The medical device of claim 1, wherein the polymer is derived from a polymer precursor selected from the group consisting of hyaluronic acid, heparin, chondroitin sulfate, pectinic acid, a carboxyl-derivatized polysaccharide, a synthetic polymer, and combinations thereof.

3. The medical device of claim 1, wherein the polymer is derived from a polymer precursor selected from the group consisting of polyhydroxy ethyl methacrylate, polyvinyl alcohol, polyacrylamide, poly (N-vinyl pyrrolidone), polyethylene oxide, hydrolyzed polyacrylonitrile, polyacrylic acid, polymethacrylic acid, polyethylene amine, a polysaccharide, and combinations thereof.

4. The medical device of claim 3, wherein the polysaccharide is selected from the group consisting of alginic acid, pectinic acid, carboxymethyl cellulose, hyaluronic acid, chitosan, cationic guar, and cationic starch, including salts, and esters, and combinations thereof.

5. The medical device of claim 1, wherein the device comprises a crosslinkable polymer having non-ionic crosslinks susceptible to hydrolysis in vivo.

6. The medical device of claim 5, wherein the non-ionic crosslinks are reversible covalent crosslinks.

7. The medical device of claim 5, wherein the polymer is crosslinked by a polyfunctional covalent crosslinking agent.

8. The medical device of claim 5, wherein the polymer is crosslinked by a covalent crosslinking agent which is a polyfunctional carbodiimide.

9. The medical device of claim 5, wherein the polymer is crosslinked by a covalent crosslinking agent which is a polyfunctional aziridine crosslinking agent.

10. The medical device of claim 5, wherein the polymer is crosslinked by a covalent crosslinking agent which is a polyisocyanate crosslinking agent.

11. The medical device of claim 5, wherein the polymer is crosslinked by a covalent crosslinking agent which is a glutaraldehyde crosslinking agent.

12. The medical device of claim 1, wherein the device includes a first segment and a second segment each having ionic crosslinks susceptible to dissolution in vivo such that the first segment and the second segment degrade in vivo at different rates.

13. The medical device of claim 12, wherein the first segment has a higher ionic crosslinking content than the second segment.

14. The medical device of claim 12, wherein the first segment has a thinner wall than the second segment.

15. The medical device of claim 12, wherein the first segment comprises a polymer crosslinked with a first ion and the second segment comprises a polymer crosslinked with a second ion.

16. The medical device of claim 15, wherein the first ion has a higher electron affinity than the second ion.

17. The medical device of claim 16, wherein the second ion is selected from the group consisting of $Mg^{2++}$ and $Ca^{2++}$.

18. The medical device of claim 17, wherein the first ion is selected from the group consisting of $Ba^{2++}$ and $Zn^{2++}$.

19. The medical device of claim 12, wherein the first segment and the second segment comprise one or more polymers crosslinked with a high affinity ion and a low affinity ion, and the first segment has a higher concentration of high affinity ion crosslinks and a lower concentration of low affinity ion crosslinks than the second segment.

20. The medical device of claim 1, wherein the device includes a first segment comprising a crosslinkable polymer having ionic crosslinks susceptible to dissolution in vivo and a second segment comprising a crosslinkable polymer having non-ionic crosslinks susceptible to hydrolysis in vivo.

21. The medical device of claim 20, wherein the device includes break point in a relatively straight section of the device proximal to a curved section of the device.

22. The medical device of claim 1, further comprising a segment comprising a non-dissolvable, non-disintegrable polymer.

23. The medical device of claim 22 wherein the non-dissolvable, non-disintegrable polymer is silicone.

24. The medical device of claim 22, wherein the segment comprising the non-dissolvable, non-disintegrable polymer is selected from the group consisting of a string, a mesh, a suture, and a braid.

25. The medical device of claim 1, further comprising a segment comprising a biodegradable polymer.

26. The medical device of claim 25, wherein the biodegradable polymer is selected from the group consisting of the polymers of glycolic acid, $\epsilon$-caprolactone, lactic acid and copolymers thereof.

27. The medical device of claim 25, wherein the segment comprising the biogradable polymer is selected from the group consisting of a string, a mesh, a suture, and a braid.

28. The medical device of claim 1, wherein the device is selected from the group consisting of a stent, a catheter, a cannula, a plug, a constrictor, a bone anchor, a plate, a rod, a seed, a capsule, a sheet, and a tube.

29. The medical device of claim 1, wherein the device is a biliary, urinary, or vascular stent.

30. The medical device of claim 1, further comprising at least one pigtail end.

31. The medical device of claim 1, wherein the device is a tissue prosthesis.

32. The medical device of claim 1, further comprising suture material as a filler.

33. The medical device of claim 1, wherein the device is seeded with cells.

34. The medical device of claim 1, further comprising a radiopaque filler.

35. The medical device of claim 34, wherein the radiopaque filler is selected from the group consisting of bismuth sub-carbonate, barium sulfate, bismuth oxychloride, tungsten, bismuth trioxide, tantalum, and combinations thereof.

36. The medical device of claim 1, further comprising an additive for medical treatment selected from the group consisting of an antiseptic, an antibiotic, an anticoagulant, a contraceptive, a nucleic acid, a protein, and a medicine.

37. The medical device of claim 36, wherein the nucleic acid is selected from the group consisting of a gene, a cDNA, a vector, an RNA molecule, an antisense molecule, a ribozyme, and a PNA molecule.

38. The medical device of claim 36, wherein the additive for medical treatment is added to only a portion of the medical device.

* * * * *